(12) United States Patent
Bost

(10) Patent No.: US 11,253,744 B1
(45) Date of Patent: Feb. 22, 2022

(54) PHYSICAL THERAPY DEVICE FOR AIDING IN JOINT MOBILITY AND RECOVERY

(71) Applicant: Aric Bost, Little Elm, TX (US)

(72) Inventor: Aric Bost, Little Elm, TX (US)

(*) Notice: Subject to any disclaimer, the term of this patent is extended or adjusted under 35 U.S.C. 154(b) by 277 days.

(21) Appl. No.: 16/354,551

(22) Filed: Mar. 15, 2019

Related U.S. Application Data

(60) Provisional application No. 62/643,853, filed on Mar. 16, 2018.

(51) Int. Cl.
*A61F 5/01* (2006.01)
*A63B 21/00* (2006.01)
*A63B 23/035* (2006.01)

(52) U.S. Cl.
CPC ...... *A63B 23/03508* (2013.01); *A61F 5/0102* (2013.01); *A63B 21/4025* (2015.10); *A61F 2005/0158* (2013.01); *A61F 2005/0165* (2013.01); *A61F 2005/0179* (2013.01)

(58) Field of Classification Search
CPC ...... A61F 2005/0158; A61F 2005/0165; A61F 2005/0179; A61F 5/01; A61F 5/0102; A61F 5/0123; A61F 5/013; A61F 2005/0137; A61F 2005/0139; A63B 23/035; A63B 23/03508; A63B 23/04; A63B 23/0494; A63B 23/12; A63B 23/1284; A63B 23/16; A63B 21/4025
See application file for complete search history.

(56) References Cited

U.S. PATENT DOCUMENTS

| | | | | |
|---|---|---|---|---|
| 5,244,455 A | * | 9/1993 | Swicegood | ........... A61F 5/0123 602/16 |
| 7,517,330 B2 | * | 4/2009 | Deharde | ............... A61F 5/0125 602/16 |
| 9,089,402 B2 | * | 7/2015 | Campbell | ............ A61H 1/0266 |

* cited by examiner

*Primary Examiner* — Keri J Nelson
(74) *Attorney, Agent, or Firm* — Leavitt Eldredge Law Firm

(57) ABSTRACT

A physical therapy device includes a brace to secure around an appendage of a person; a first locking device connected to a portion of the brace via a rivet joint, the first locking device having a gear; a pawl positioned to engage with the gear; a spring connected to the pawl to provide tension to the pawl; and a lock to release the pawl from the toothed gear; the first locking device is positioned next to a joint of the appendage when worn; the first locking device allows for single direction movement of the joint; and the first locking device is to release the joint via the lock.

4 Claims, 5 Drawing Sheets

PHYSICAL THERAPY DEVICE FOR AIDING IN JOINT MOBILITY AND RECOVERY

BACKGROUND

1. Field of the Invention

The present invention relates generally to physical therapy systems, and more specifically, to a physical therapy device for aiding in joint recovery, mobility, and flexibility.

2. Description of Related Art

Physical therapy systems are well known in the art and are effective means to help heal injuries. For example, FIG. 1 depicts a flowchart 101 of a conventional method of physical therapy for joint recovery. Conventionally, a person who has injured a joint, such as a finger, elbow, or knee, must work to regain flexibility in the joint, as shown with box 103. The person (either on their own or with a physical therapy professional), will work to bend the joint as far as they can and either hold in that position, or receive aid from the professional to help hold the joint in that position, as shown with boxes 105, 107. When the pain becomes too much or the person fatigues, they will release the joint to a resting position, as shown with boxes 109, 111.

This type of physical therapy takes many hours of dedication over a long period of time. Many times, even simple injuries can take years to fully heal. One reason for this, is that the person may not have the assistance they need to always work their joints in the required way, i.e. bending and holding to increase flexibility. Therefore, the person is limited in the amount of time and effort that they can put into their recovery.

Accordingly, although great strides have been made in the area of physical therapy systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
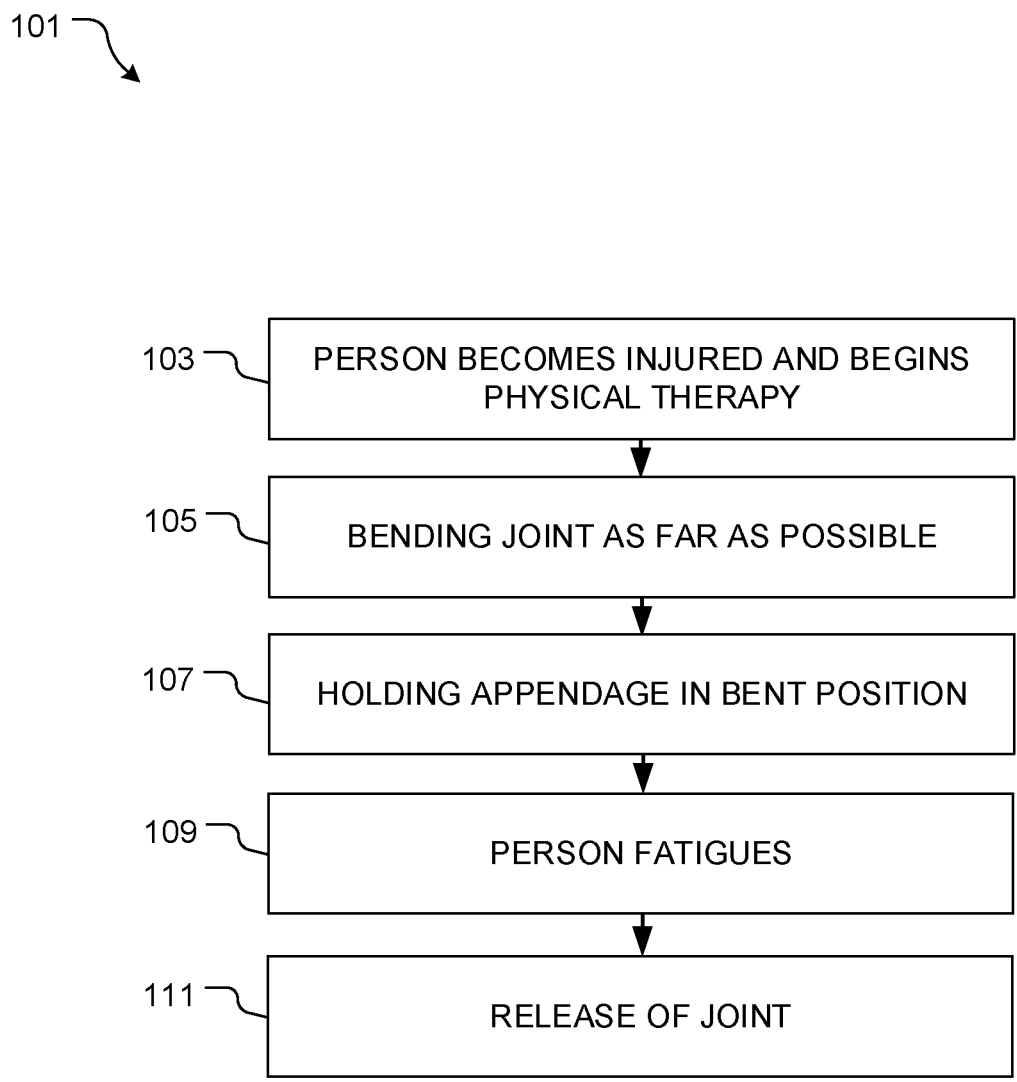
FIG. 1 is a flowchart of a conventional method of physical therapy.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional physical therapy systems. Specifically, the present invention uses a locking device allowing for a single direction of movement of the joint of an appendage, thereby providing a means for a person to efficiently work a joint without assistance. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
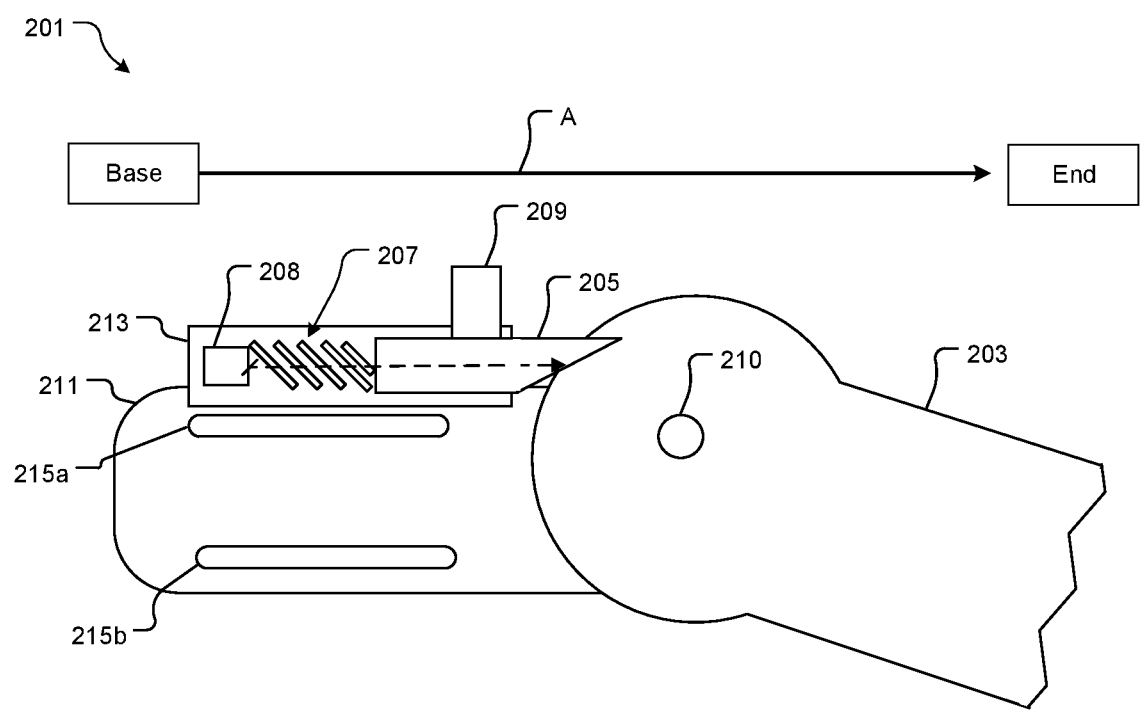
FIG. 2 is a front view of a locking device in accordance with a preferred embodiment of the present application.
Figure 4:
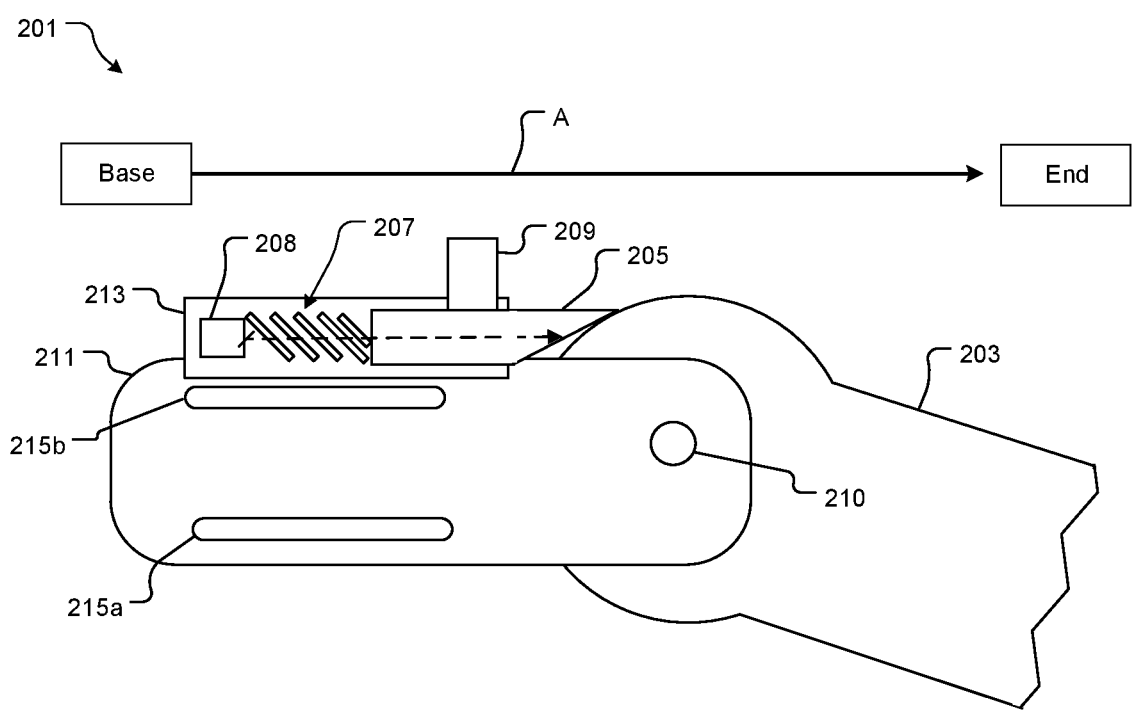
FIG. 4 is a rear view of the locking device of FIG. 2.
Figure 5:
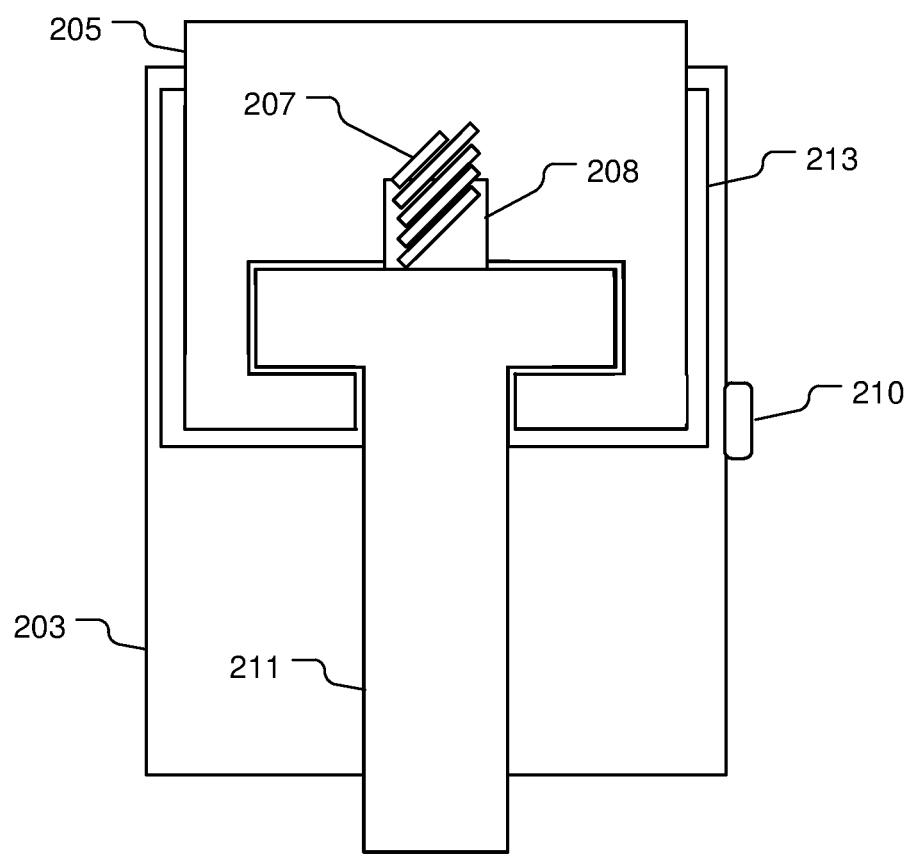
FIG. 5 is a side view of the locking device of FIG. 2.

Referring now to the drawings wherein like reference characters identify corresponding or similar elements throughout the several views, FIGS. 2, 4, and 5 depict front, rear, and side views respectively of a locking device 201 to be incorporated into a physical therapy device 301 in accordance with a preferred embodiment of the present application. It will be appreciated that device 201 overcomes one or more of the above-listed problems commonly associated with conventional physical therapy systems.

In the contemplated embodiment, device 201 includes a gear 203, such as a toothed gear, configured to engage with a spring-loaded pawl 205. The pawl is configured to engage with the gear 203 to allow for a single direction of movement of the gear. A spring 207 is engaged with the pawl to retain force exertion to ensure that the single directional movement is achieved. In the preferred embodiment, a stop 208 can be used to position the spring in the correct orientation.

Figure 3:
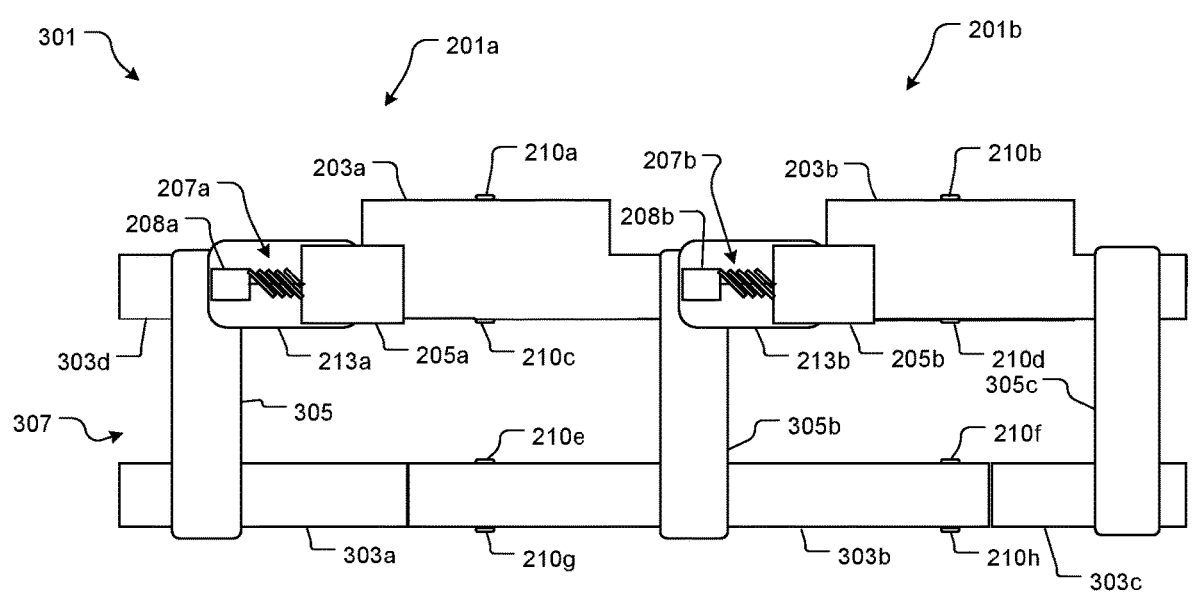
FIG. 3 is a top view of a physical therapy device with two locking devices as shown in FIG. 2 incorporated therein in accordance with a preferred embodiment of the present application.

As further shown in the various figures, a lock 209 extends from pawl 205 allowing for the user to release the pawl from the gear by applying backwards pressure on the lock. Device 201 further includes a support bracket 211 to allow for engagement of the device 201 with a brace (as shown in FIG. 3) to thereby secure to an appendage of the user. Bracket 211 is secured to gear 203 via a rivet joint 210, to allow for rotation of the gear and bracket relative to one another. It should be appreciated that the gear 203 is positioned at an angle, wherein manual rotation of the gear is possible.

It should be appreciated that device 201 can come in a variety of sizes, thereby providing devices that can be used for all appendages, including legs, arms, and fingers.

In some embodiments, a housing 213 encompasses the spring and a portion of the pawl and lock to improve safety and aesthetical appearance. Further, bracket 211 can include slots 215a-b for receiving straps, such as hook and loop fasteners, for creating a brace to secure to a user's appendage.

As shown with arrow A, the locking device 201 is to be positioned at a user's joint, from a base to the end of the joint, regardless of the size of the joint. During use, the user begins to bend the joint, such as their finger, and as the joint is bent, the gear engages with the pawl to prevent backwards (unbending) movement of the joint. This allows the user to stop bending at a desired tension, either based on predetermined instructions from a professional, or based on pain. The locking device aids the user in holding the bend until the user releases the pawl via lock 209, thereby releasing the user's appendage.

In FIG. 3, one example of a therapy device 301 is shown with two locking devices 201a, 201b, being configured for a finger, having two joints. It should be appreciated that locking device 201 can be incorporated to variously structured braces for use, as is necessary for braces for different appendages.

As shown, each locking device includes the features discussed above, including gears 203a, 203b, such as toothed gears, engaged with spring loaded pawls 205a, 205b, the spring loaded pawls being in further connection with springs 207a, 207b and stops 208a, 208b and contained in housings 213a, 213b.

As further shown in FIG. 3, a plurality of rivet joints 210a-h are used to connect a plurality of support brackets 303a-d to one another and to gears 203a-b, thereby allowing for pivoting movement of the various components relative to one another. In this embodiment, one or more perpendicular support beams 305a-c connect brackets to provide a channel 307, through which the appendage (finger) is placed. It should be understood that the locking devices align with the joints of the finger to aid in physical therapy exercise.

It should be appreciated that one of the unique features believed characteristic of the present application is locking device 201 configured to provide single direction movement of a joint, thereby aiding a user in physical therapy activities involving joint recovery.

In FIG. 4, a side view of a locking device 201, with the various components discussed herein, is shown for further clarity and understanding. It should be appreciated that the materials of device 201 can vary as aesthetical, functional, or manufacturing considerations require.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A physical therapy device, comprising:
    a support bracket configured to secure around an appendage of a person;
    a gear pivotally secured to the support bracket;
    a housing secured to the support bracket, the housing houses a first locking device connected to a portion of the support bracket, the first locking device having:
        a pawl positioned to engage with the gear, the pawl is configured to releasably engage with the gear such that the gear is retained within a fixed position while in a locked position;
        a spring connected to the pawl and configured to provide tension to the pawl; and
        a lock configured to release the pawl from the gear and configured to retain the pawl against the gear while in the locked position;
    wherein the first locking device is positioned next to a joint of the appendage when worn;
    wherein the first locking device allows for single direction movement of the joint; and
    wherein the first locking device is configured to release the joint via the lock.

2. The device of claim 1, further comprising:
    a second locking device connected to a second portion of the support bracket via a second rivet joint;
    wherein the second locking device is positioned next to a second joint of the appendage when worn.

3. The device of claim 1, wherein the first locking device further comprises:
    a support bracket configured to attach to the support bracket.

4. The device of claim 1, wherein the support bracket further comprises:
    at least two parallel support brackets connected via one or more perpendicular support bars;
    wherein the at least two parallel support brackets and one or more perpendicular support bars form a channel through which the appendage is capable of being received.

* * * * *